(12) United States Patent
Murias

(10) Patent No.: US 7,611,355 B2
(45) Date of Patent: Nov. 3, 2009

(54) MANUAL DRIVER FOR IMPLANT DRILLS AND METHOD OF DENTAL IMPLANTATION

(76) Inventor: German L. Murias, 7000 W. 12$^{th}$ Ave., Suite No. 7, Hialeah, FL (US) 33014

( * ) Notice: Subject to any disclaimer, the term of this patent is extended or adjusted under 35 U.S.C. 154(b) by 29 days.

(21) Appl. No.: 11/698,231

(22) Filed: Jan. 25, 2007

(65) Prior Publication Data

US 2007/0178427 A1  Aug. 2, 2007

Related U.S. Application Data

(60) Provisional application No. 60/762,730, filed on Jan. 27, 2006.

(51) Int. Cl.
- *A61C 3/00* (2006.01)
- *A61C 3/02* (2006.01)
- *A61C 8/00* (2006.01)
- *A61C 5/00* (2006.01)
- *A61C 5/04* (2006.01)

(52) U.S. Cl. .................. 433/174; 433/215; 433/225; 433/201.1; 433/173; 433/141; 433/175; 433/165

(58) Field of Classification Search .............. 433/141, 433/173–174, 165, 215–225

See application file for complete search history.

(56) References Cited

U.S. PATENT DOCUMENTS

| | | | | |
|---|---|---|---|---|
| 5,538,424 A | * | 7/1996 | Gelb | 433/72 |
| 5,997,298 A | * | 12/1999 | Nowak | 433/165 |
| 6,146,138 A | * | 11/2000 | Dalmau | 433/141 |
| 6,547,562 B2 | * | 4/2003 | Kumar | 433/165 |
| 6,604,945 B1 | * | 8/2003 | Jones | 433/173 |
| 6,863,529 B2 | * | 3/2005 | Strong et al. | 433/165 |
| 7,241,144 B2 | * | 7/2007 | Nilo et al. | 433/174 |
| 2002/0009692 A1 | * | 1/2002 | Ashman | 433/173 |
| 2002/0094508 A1 | * | 7/2002 | Lorenzi | 433/165 |

* cited by examiner

*Primary Examiner*—Cris L Rodriguez
*Assistant Examiner*—Yogesh Patel
(74) *Attorney, Agent, or Firm*—Melvin K. Silverman; Yi Li

(57) ABSTRACT

A manual driver for a dental implant drill or other dental implant tools and the method of use for preparing for dental implantation are provided. The manual driver includes a handle, an extension shank and a chuck having an axial channel configured to receive and interlock an implant drill, and a fastening screw transverse to the axial channel. The method of manual preparation for dental implantation using the manual driver has a high precision, and reduces the risk of bone cracking caused by vibration of motor-driven drilling. The manual drilling method provides better tactile sensation and drilling control to the dentist. Further, the method avoids drilling irrigation, allows collection of virgin bone tissue from the drills, and reintroduces the collected bone tissue in the receiving bore to promote bone regeneration after the implantation.

5 Claims, 4 Drawing Sheets

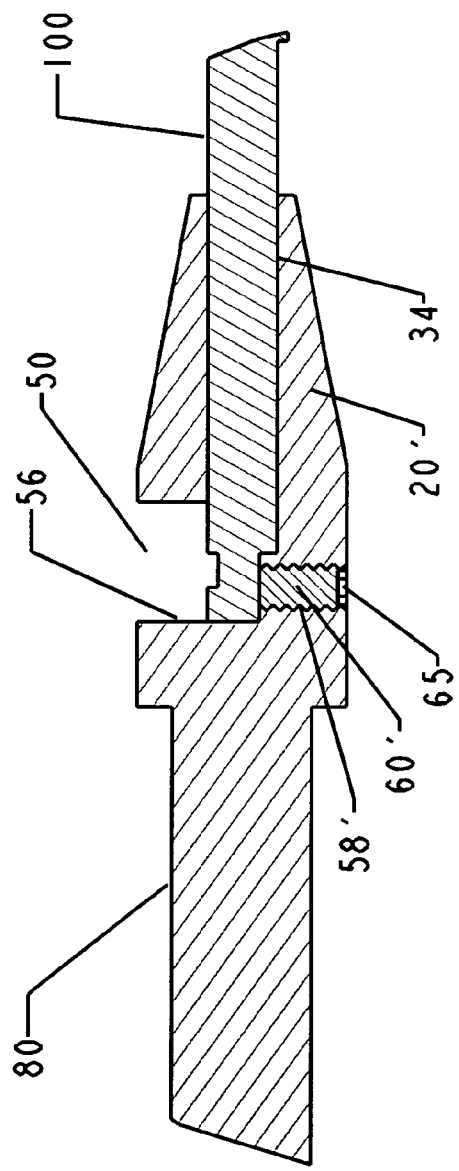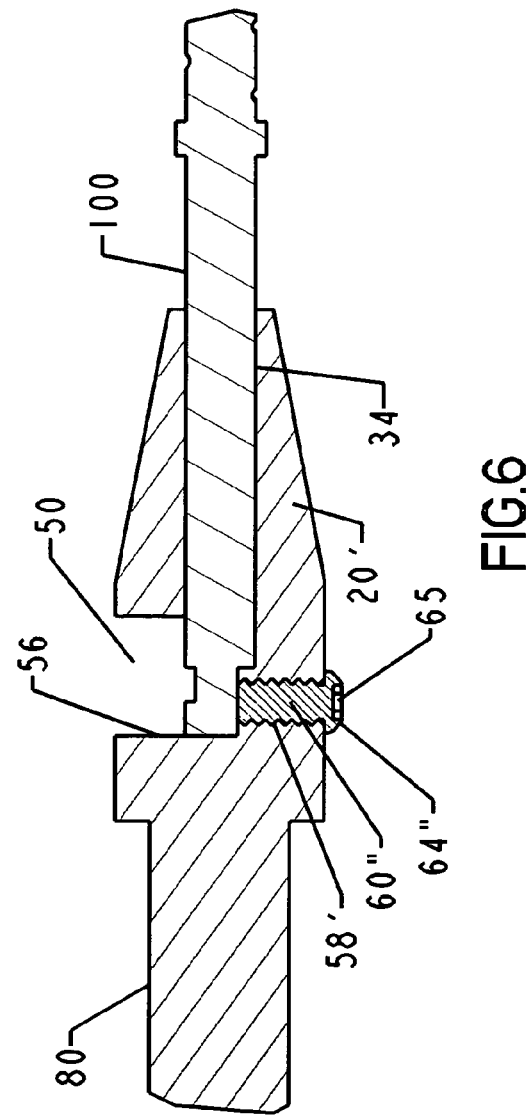

MANUAL DRIVER FOR IMPLANT DRILLS AND METHOD OF DENTAL IMPLANTATION

CROSS REFERENCE TO RELATED APPLICATION

This application claims the benefit under 35 USC 119 (e) of the provisional patent application Ser. No. 60/762,730, filed on Jan. 27, 2006, which is hereby incorporated by reference in its entirety.

FIELD OF THE INVENTION

The present invention relates to a manual driver configured to receive and drive an implant drill or other dental implant tools, and the methods of manual preparation for dental implantation using the manual driver.

BACKGROUND OF THE INVENTION

Currently, in all dental implantation procedures drilling is performed using motor-driven drilling. Motor-driven drilling has certain advantages, such as fast and less labor demanding, however, it also has various drawbacks. For example, in the process of preparing dental implantation, drilling is frequently made on a location which has very thin bones. Since motor-driven drilling causes vibrations, at the area where bone is very thin it tends to cause cracking of the bone and renders implantation impossible. Furthermore, motor-driven drilling provides one directional drilling, i.e., clockwise, which generates more pressure on the surrounding bone, hence, this also poses a higher risk of bone cracking, as well as causes more trauma to the patient. Consequently, in some areas or situations implantations have been considered not permissible because of the risks associated with the drilling.

Furthermore, because of the high speed and the vibration of motor-driven drilling, it requires substantial skills and experiences in proper control of the angulation of drilling. Often, a correction of drilling angulation needs to be made when the bore generated is not precisely in the required angulation, particularly in an area, such as at the front of the mouth, where a high precision is required. Additionally, using motor-driven drilling, the dentists have a limited tactile sensation about the surrounding bone structures in the process of drilling. Clinically, a commonly seen accident is the drill penetrating into the sinus, the floor of the nose, or bone cortex (outer layer of bone) in the preparation process for implantation in the upper jaw of the patient.

Moreover, motor-driven drilling generates heat, therefore, water cooling of the drill and the bore is required. This is typically done using an irrigation device adjacent to the drill. With irrigation, frequently the cooling water is accumulated in the patient's throat, the surgical procedure has to be stopped until the patient clears his throat. This interrupts the process and can be dangerous during drilling. Moreover, the cooling water also causes a further disturbance of the wound.

On the other hand, it has been found in the recent years that the bone tissue collected from the threads of the implant drills immediately after the drilling can be used to enhance bone regeneration around the implant. Typically, the dentist collects the bone tissue from the threads of the implant drills used in drilling, after the implant is placed inside the bore, the collected bone tissue is placed around the implant before suturing the wound. However, in the presence of irrigation, the bone tissue collected is washed by the cooling water. Typically, a dentist harvests bone tissue using a bone trap connected to a suction hose, and sucks away the cooling water and collects bone tissue on a filter in the trap. Such a process can cause dehydration of the bone tissue, which affects the quality of the collected bone tissue, and bone regeneration surrounding the implant.

Therefore, it is desirable to provide improved tools and methods to solve the problems described above, and achieve a better precision and control of the dental implantation process. The present invention addresses this long felt need in the field.

SUMMARY OF THE INVENTION

In one aspect, the present invention is directed to a manual driver for an implant drill or other dental implant tools. The manual driver comprises a chuck having an axial channel with an opening at a distal end of the chuck and a stop in a proximal portion of the chuck, and a fastening screw transverse to the axial channel adjacent to the stop, the axial channel including an abutment portion for interlocking with a shaft of the implant drill; an extension shank integral with and extending from the proximal portion of the chuck along a longitudinal axis of the manual driver; and a handle extending from a proximal end of the extension shank along the longitudinal axis. The proximal portion of the chuck includes a threaded transverse bore disposed at the abutment portion of the axial channel for receiving the fastening screw.

In a further aspect, the present invention is directed to a manual preparation method for dental implantation. In one embodiment, the method comprises the steps of providing a manual driver comprising a handle and a chuck configured to receive and lock an implant drill therein; securing a shaft of a first implant drill into the chuck of the manual driver; manually driving the first implant drill at a selected location to create an initial bore by turning the driver clockwise and counter clockwise until the first implant drill reaching a desired depth; taking a x-ray image of the initial bore to confirm proper angulation of the initial bore; manually driving one or more implant drills that has an increased diameter from the first implant drill using the manual driver to expand the initial bore by turning the driver clockwise and counter clockwise until obtaining a final bore having a desired diameter; removing the implant drills, and collecting bone tissue on threads of each of the implant drills into a sterilized container; placing collected bone tissue back into the final bore; and placing the dental implant into the final bore that is filled with the collected bone tissue. Preferably, after the first drilling, the first implant drill is remained in the initial bore for taking the x-ray image, and to prevent bleeding.

In a further embodiment, the present invention is directed to a method of immediate dental implantation. The method combines extraction of a selected tooth and implanting the dental implant in one surgical procedure. The preparation for implantation is substantially the same as the process described above, except that the drilling starts with the cavity generated from extraction of the tooth.

The manual driver and the method of the present invention have various advantages over the existing motor driven drilling method, which will become apparent from the hereinafter set forth Detailed Description of the Invention and Claims appended herewith.

BRIEF DESCRIPTION OF THE DRAWINGS

FIG. 5 is a fragmentary axial cross-sectional view along the longitudinal axis of said manual driver, showing a variation of the transverse bore and an Allen head screw.

FIG. 6 is a fragmentary axial cross-sectional view along the longitudinal axis of said manual driver, showing the enlarged screw head being disposed outside of the transverse bore.

It is noted that in the drawings like numerals refer to like components.

DETAILED DESCRIPTION OF THE INVENTION

Figure 1:
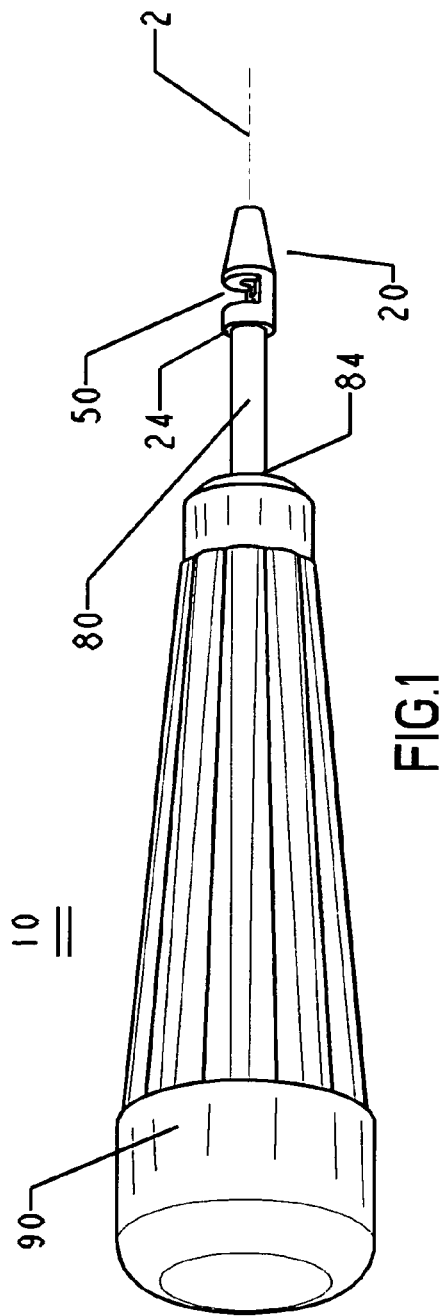
FIG. 1 is a perspective view of the manual driver.

In one aspect, the present invention provides a manual driver for dental implant drills or other dental implant tools.

With reference to FIGS. 1 thru 4B, in one embodiment, manual driver 10 comprises a chuck 20, an extension shank 80 connected to a proximal end 24 of chuck 20 and a handle 90 connected to a proximal end 84 of extension shank 80, all coaxially aligned on longitudinal axis 2 of manual driver 10.

In the embodiment shown, chuck 20 has a conical distal portion 30 which tapers toward distal end 22 of chuck 20, and a generally cylindrical proximal portion 40. Distal portion 30 has an axial channel 34 extending through the entire distal portion, and further into proximal portion 40 as described hereinafter. Axial channel 34 has an opening 36 at distal end 22 of chuck 20. It should be understood that the distal portion can also have other suitable shapes, such as cylindrical and elliptical.

Figure 2:
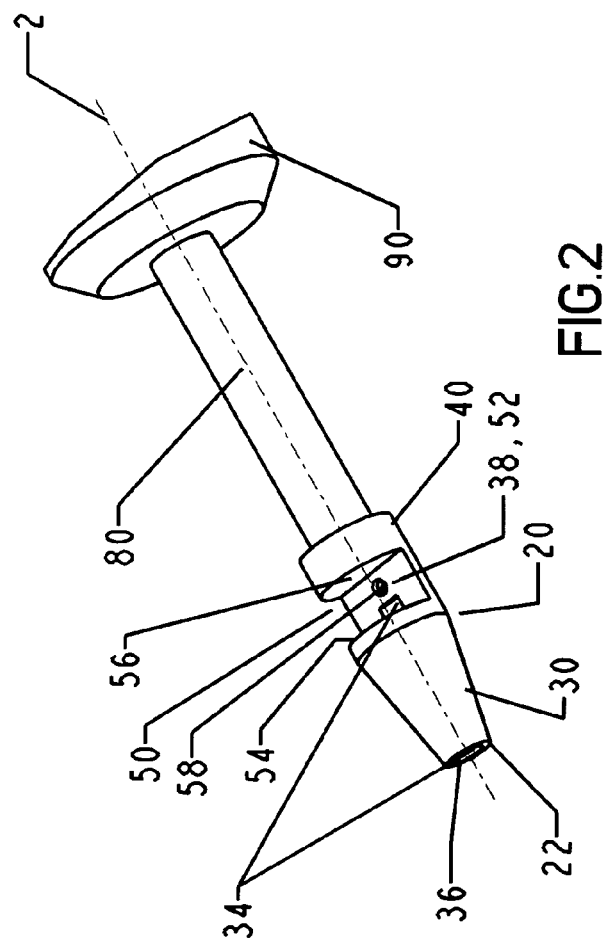
FIG. 2 is an enlarged perspective view of the chuck and the extension shank of the instant manual driver.

In the embodiment shown, proximal portion 40 has a U-shape like cut-out 50. The proximal end 56 of cut-out 50 forms a stop, and distal end 54 of cut-out 50 intersects with axial channel 34, therefore, the lower portion of the axial channel 34 extending beyond distal end 54 of cut-out 50 into proximal portion 40, as shown in FIGS. 2 and 4A. The bottom of cut-out 50 forms a planar surface 52 in parallel with longitudinal axis 2 of manual driver 10. In the structure shown, planar surface 52 functions as an abutment portion 38 of axial channel 34 for interlocking with the shaft of an implant drill, as more fully described hereinafter.

A threaded transverse bore 58 is disposed transverse to the longitudinal axis 2 and intersecting with planar surface 52. Disposed within transverse bore 58 is a fastening screw 60, with a screw head 64 adjacent to the periphery of chuck 20, in other words, away from planar surface 52 of cut-out 50, as shown in FIG. 4A.

Figure 4:
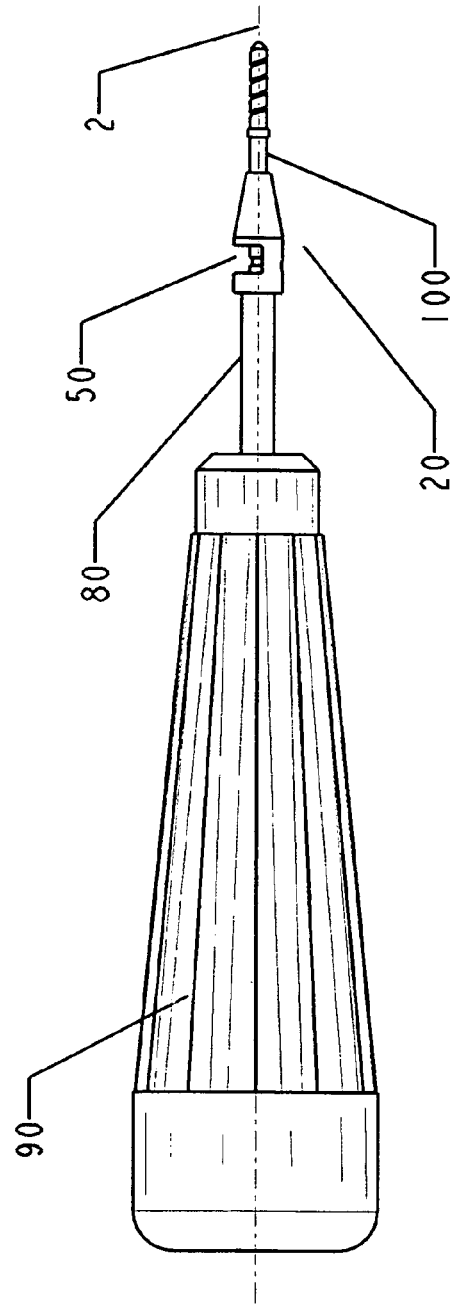
FIG. 4 is a side view of the manual driver, including an implant drill secured therein.
Figure 4A:
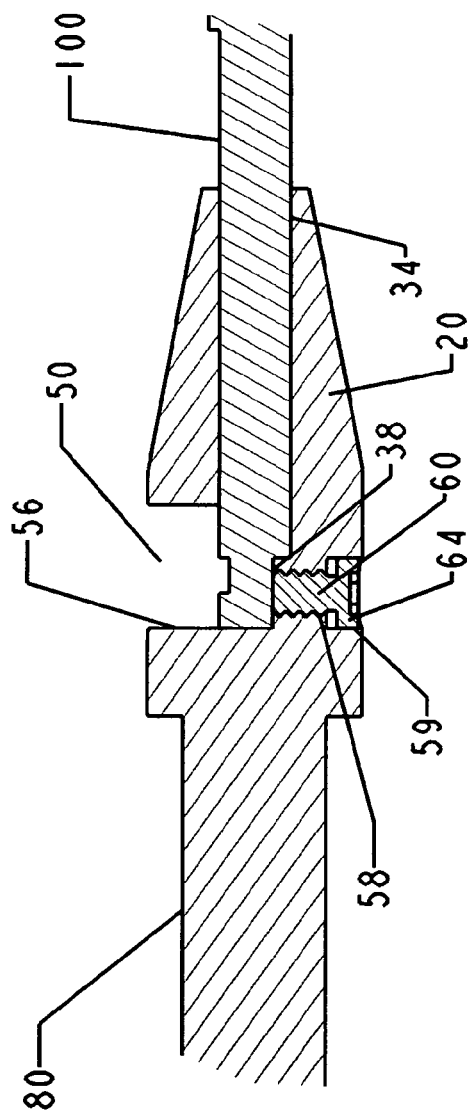
FIG. 4A is a fragmentary axial cross-sectional view along the longitudinal axis of said manual driver.
Figure 4B:
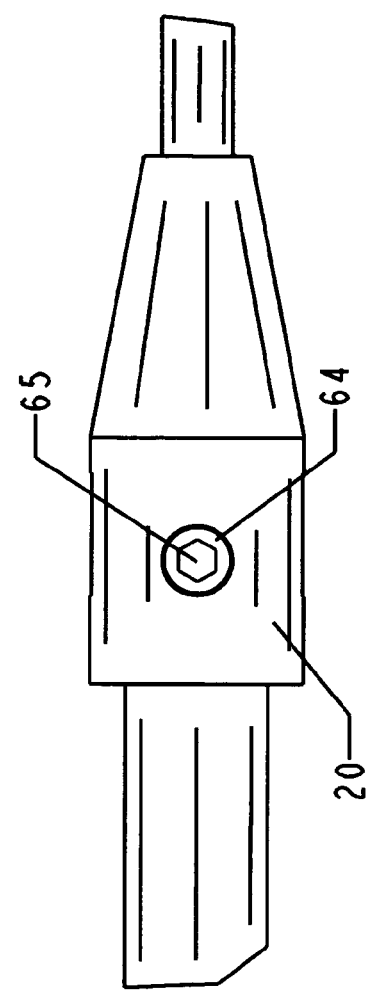
FIG. 4B is a bottom view of the chuck shown in FIG. 4.

As can be seen in FIGS. 4 and 4A, cut-out 50 renders visible the proximal portion of the shaft of an implant drill when the shaft is secured to manual driver 10. This helps the dentist to ensure that the implant drill, or other implant tools, is in position. However, it should be understood that cut-out 50 is optional. In the absence of cut-out 50, abutment portion 38 can be in a form of a step up planar platform adjacent the inner end of axial channel 34. In this case, the inner end of axial channel 34 is the stop.

Figure 3:
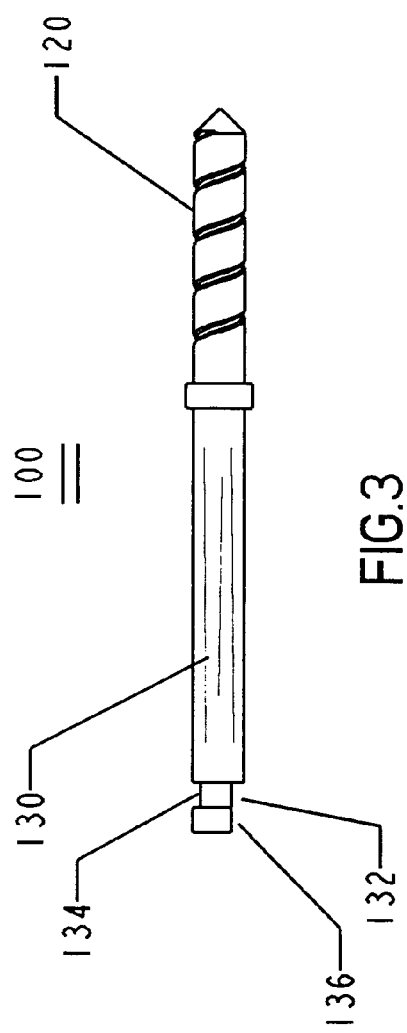
FIG. 3 is an example of a commercial available implant drill that may be used with the manual driver of the present invention.

FIG. 3 shows a commonly used implant drill 100, which is commercially available from various manufacturers. Implant drill 100 has a threaded drill head 120 and a shaft 130. Shaft 130 is cylindrical and the neck portion 136 of shaft 130 is stepped to provide a recess 132 therein. Typically, there is a transverse groove 134 in communication with recess 132.

When in use, neck portion 135 of implant drill 100 is inserted into axial channel 34 through opening 36 all the way to the proximal end 56 of cut-out 50, recess 132 of shaft 130 is disposed on planar surface 52, i.e., abutment portion 38 of axial channel 34, therefore, abutment portion 38 and recess 132 of shaft 130 are interlocked with each other. As such, rotation of manual driver 10 causes drill 100 to rotate. It is noted that groove 134 is provided for further interlocking with some drill holders, it is not required when the drill is used with the instant manual driver.

In addition to the interlocking mechanism between abutment portion 38 of axial channel 34 and recess 132 of shaft 130, a fastening screw 60 is used to fasten shaft 130 of implant drill 100 in the position. As such, implant drill 100 is firmly secured in manual driver 10, and no sliding or wobbling within the driver occurs when it is used in a surgical procedure. The stability of the implant drill within the instant manual driver is critically important, because the success of an implant replies on the precision of the drilling. Any wobbling of the implant drill, or implant tools, could cause errors in angulation and desired structure of the bore, and hence cause improper positioning of the dental implant or improper interface with the surrounding bone tissue.

FIG. 4A shows a cross-sectional structure of threaded transverse bore 58 and fastening screw 60 in one embodiment. As shown, threaded transverse bore 58 has a recess 59 at the outmost end thereof, adjacent to the periphery of chuck 20, and screw 60 has a screw head 64 disposed within recess 59. When it is tightened, screw head 64 does not protrude from chuck 20, therefore, the chuck has a smooth exterior surface. Fastening screw 60 can be tightened using a screw driver by engaging with a hexagonal opening 65 on screw head 64. Hexagonal opening 65 is compatible with standard dental screw drivers, therefore, more convenient to the dentist. However, other structure, such as a slot can also be used on the screw head. Typically, fastening screw 60 has a relatively small diameter, for example about 1.3 mm. Therefore, a screw head with an enlarged diameter can be easier for the dentist to work with, and is more durable because the implant drill is changed frequently, from surgery to surgery and can be several times within one surgery.

FIG. 5 illustrates an alternative embodiment, wherein an Allen head screw 60' is used. In this situation, threaded transverse bore 58' of chuck 20' does not have the recess, however, the screw head is disposed within threaded transverse bore 58'. FIG. 6 illustrates a further alternative embodiment, wherein chuck 20' includes a threaded transverse bore 58' and a fastening screw 60" has a longer stem with a screw head 64" disposed outside the periphery of chuck 20'.

In addition to implant drill 100, various commercially available dental implant tools, such as rotational bone expanders, bone Trephine drills, tissue punches, have the same latch type neck structure on the shaft of the tools, as shown in implant drill 100 in FIG. 3. These tools can be used with the manual driver 10 of the present invention.

Preferably, chuck 20, extension shank 80 and handle 90 are integrally connected. Chuck 20 and extension shank 80 are preferably made of stainless steel. However, other suitable materials can also be used for the chuck and extension shank, such as titanium and high density plastics. Preferably, handle 90 has an ergonomic shape, such as the structure shown in FIG. 1, to support stable hand gripping. The exterior of the handle can further include grooves to prevent sliding of the hand. Preferably, portion of the handle, such as the exterior portion, is made of a suitable plastic material which has a lighter weight than metal. Therefore, the manual driver is not too heavy for the dentist to operate with freedom and comfort.

In a further aspect, the present invention provides methods of using the manual driver for dental implant procedures.

In one embodiment, the method is directed to a manual preparation process for dental implantation. The method is described herein according to the sequence of the process steps using manual driver 10. First, a manual driver 10 is provided, and a first implant drill is secured into chuck 20 by inserting the shaft of the first implant drill all the way to stop 54 and tightening fastening screw 60. Then, the first implant drill is manually driven into a selected location in a patient's mouth to create an initial bore by turning manual driver 10 back and forth, i.e., clockwise and counter clockwise, until the first implant drill reaching a desired depth. Herein, the bore created by drilling is also referred to as osteotomy site. At this stage, manual driver 10 is removed from the shaft of the first implant drill by loosening the fastening screw 60, while the first implant drill is left within the initial bore. Then, a x-ray image of the initial bore is taken to confirm proper angulation of the initial bore. Upon confirming the proper angulation, the first implant drill is removed from the initial bore by turning back and forth, and then the bone tissue on threads of the first implant drill is collected in a sterilized container. At this stage, if angulation of the initial bore is improper, further drilling with the first implant drill to correct the angle of the initial bore is performed. After the initial drilling, the initial bore is expanded using one or more implant drills that have a sequentially, or stepwise, increased diameter from the prior implant drill. In each drilling, the implant drill is secured into manual driver as described above, and the drilling is performed manually by turning the driver clockwise and counter clockwise. In this step, typically one to three implant drills can be used until obtaining a final bore that has the desired diameter. After each step of drilling, the implant drill is retrieved from the bore, and the bone tissue on threads of the implant drills is collected into the sterilized container. Once the final bore is obtained, the collected bone tissue is placed back into the final bore, using a specula or other suitable tools. After filling, a plugger can be inserted to push the bone tissue down. Typically, about 30% to about 50% of the interior of the final bore is filled with the collected bone tissue. Then, a predetermined dental implant is placed, using the conventional method, into the final bore that is filled with the collected bone tissue. When the implant is in place, the area around the top of the dental implant is further packed with the collected bone tissue. Then, an absorbable collagen wound dressing is applied, and the gum is sutured according to the requirement of the subsequent implant procedures.

Furthermore, after the initial drilling one or more rotational bone expanders can be used in addition to a minimal amount of drilling to expand the diameter of the bore. Using rotational bone expanders can effectively expand the diameter of the bore with minimal loss of bone tissue and effectively increase bone density around the bore, which has been found to produce more stable anchoring of the implant, and enhance bone regeneration at the interface between the implant and the surrounding environment.

Moreover, the collected bone tissue can also be mixed with human allograft tissue, for example, Grapton® demineralized bone matrix available commercially from Osteotech Inc. (Eatontown, N.J.), prior to placing into the final bore. Preferably, the mixture can have a ratio from about 1:2 to about 2:1 between the two components. In several dental implant procedures performed using the instant manual driver and the method, a 1:1 mixture of the collected bone tissue and Grapton® demineralized bone matrix is used. Using the mixture helps to achieve the desired bone volume. Furthermore, it has been found that the mixture lasts longer in the osteotomy site, which is more effective for facilitating local bone regeneration.

The method of the present invention has various advantages in comparison to the traditional process of preparing the bore using motor-driven drilling, which are described in detail below.

First, motor-driven drilling has a very high speed, typically from about 400 to about 2,000 rpm, which causes vibrations in the surrounding bone. At the area where bone is very thin, motor-driven drilling tends to cause cracking of the bone and renders implantation difficult or impossible. Furthermore, motor-driven drilling provides one directional drilling, i.e., clockwise, which generates pressure on the surrounding bone, causes more trauma to the patient and poses risks of bone cracking. Using manual drilling, as provided above with the instant manual driver and the method, the drilling does not cause vibration. Moreover, turning the drill clockwise and counter clockwise, manual drilling generates less pressure in the surrounding bone. Consequently, it has a substantially lower risk for cracking the bone. It has been found that in several situations where the implantations were not permissible with the traditional motor-driven drilling because of the risks associated with the drilling, the implantations were successfully performed using the manual driver and the method of the present invention.

Second, using the instant manual driver the precision of the drilling can be better controlled. With motor-driven drilling, prior to entering into the bone, the drill head tends to wobble on the exterior surface of the bone, which renders the control of the location and angulation difficult. Furthermore, during drilling the vibration also causes difficulty in controlling angulation. On the other hand, manual drilling is substantially slower, it does not cause vibration, and the speed can be well controlled by the dentist. As such, it is easier to achieve a proper angulation of the bore, which ultimately results in a more successful implantation.

Furthermore, it has been found that using the instant manual driver, the dentist has a better tactile sensation during the drilling process. When the dentist senses a density change or more difficult to proceed with drilling, this indicates a local structural change, such as in the situation when the drill is approaching the sinus, or the floor of the nose. Under such circumstances, the dentist can stop drilling to exam the situation and timely adjust the process. Because of the high speed and vibration associated with the motor-driven drilling it is difficult for the dentist to sense the structural change, and hence, difficult to respond timely without substantial experiences. Clinically, it happens often that motor-driven drilling causes penetration into the sinus, the floor of the nose, or bone cortex in the process of preparing implantation in the upper jar. Using the manual driver and method of the present invention, the risk of accidents due to lack of sensation and control from the dentist is reduced substantially. Even with a less experienced professional, those difficult situations can be better controlled with manual drilling.

Third, motor-driven drilling generates heat because of its high speed, therefore, water cooling of the drill and the bore is required. This is typically done using an irrigation device adjacent to the drill. In the presence of irrigation, it is more difficult to collect bone tissue, and the bone tissue collected is washed by the cooling water. Irrigation further causes additional disturbance of the wound. Moreover, irrigation can interfere the dentist's operation because of the water spiting from the drill. Sometimes, the cooling water is accumulated in the patient's throat, the drilling has to be stopped to allow the patient to clear his throat. With a motor-driven drilling procedure, a dentist typically harvests bone tissue using a bone trap connected to a suction hose, and sucks away the cooling water and collects bone tissue on a filter in the trap. This method can cause dehydration of the bone tissue, which affects the quality of bone tissue, and bone regeneration around the implant.

Substantially different from the motor-driven drilling process, the manual drilling method of the present invention does not generate heat, therefore, no cooling water is used. Consequently, it is easier to harvest the bone tissue from the implant drills, and the bone tissue collected is virgin bone tissue, meaning not washed, or contaminated by non-natural materials, such as the cooling water, and not dehydrated. Because the collected bone tissue is substantially natural, after placing it back into the bore, it is more effective in promoting local bone regeneration after the implantation. Furthermore, without heating the very costly implant drills can also be used longer.

Additionally, the instant method fills the bone tissue into the bore prior to placing the implant. This ensures the bone tissue filling in all available spaces between the implant and the bore, and hence is more effective in enhancing local bone regeneration after the implantation.

Fourth, traditionally, after the initial drilling the first implant drill is removed from the initial bore, then a pin is inserted into the bore as an indicator for the x-ray image. In the instant method, the first implant drill is remained within the initial bore after the initial drilling without removal, it has been found that it reduces bleeding within the bore, therefore, no cleaning of blood, either by rinsing or using gauze, is required. This reduces the process steps, and reduces the agitation of the surrounding tissue. The instant manual driver can be easily separated from the implant drill by loosening the fastening screw and sliding the chuck away from the shaft of the implant drill.

Based on the above description, it can be appreciated that the instant method provides better precision and control in preparation for dental implantation, poses less stress and trauma to the surrounding tissue, and reduces risks associated with drilling. Furthermore, it allows collection of virgin bone tissue for bone grafting at the implant site.

In a further embodiment, the method is directed to an immediate dental implantation process. Herein, the term of "immediate dental implantation process" refers to a surgical procedure wherein the implant is placed immediately after the extraction of a tooth. In contrast, the more commonly used implant process involves two separate surgical procedures, one for extraction and one for implantation, which is typically arranged two to three months later after the cavity formed from the extraction is no longer present because of bone regeneration.

In this embodiment, the method steps are the same as those described above except the followings. A selected tooth is extracted using the conventionally method, which results in a cavity that typically has an oval shape, not cylindrical. The wall of the cavity is cleaned and rinsed. At the initial drilling, the first implant drill is manually drilled beyond the bottom of the cavity, in other words, the initial bore is deeper. Then, all previously described method steps are used in this process. The final bore generated may not be perfectly cylindrical, therefore, certain portions of the wall of the final bore may not be in direct contact with the dental implant. However, because the collected bone tissue from the drilling is filled into the final bore, when the dental implant is placed in, the collected bone tissue fills in the space between the implant and the wall of the final bore. Therefore, the surface of the dental implant is completely surrounded by bone tissue, either by the wall of the final bore, or by the collected bone tissue from the drilling.

It has been found that using the manual driver and method of the present invention, the implantation process is simplified and easier to control, and hence the surgery is faster. More importantly, the risks associated with the surgery are substantially reduced, and the patients recover faster.

While there has been shown and described the preferred embodiment of the instant invention it is to be appreciated that the invention may be embodied otherwise than is herein specifically shown and described and that, within said embodiment, certain changes may be made in the form without departing from the underlying ideas or principles of this invention as set forth in the Claims appended herewith.

What is claimed is:

1. A manual preparation method for dental implantation comprising the steps of:
   (a) providing a manual driver comprising a handle and a chuck having an axial channel along a longitudinal axis of said manual driver, configured to receive and lock an implant drill therein;
   (b) securing a shaft of a first implant drill into said axial channel in said chuck of said manual driver, with said first implant drill, said chuck and said handle all aligned along said longitudinal axis of said manual driver;
   (c) manually driving said first implant drill at a selected location to create an initial bore by turning said driver clockwise and counter clockwise until said first implant drill reaching a desired depth;
   (d) removing said manual driver from said shaft of said first implant drill, and leaving said first implant drill within said initial bore for taking x-ray image and preventing bleeding;
   (e) taking a x-ray image of said initial bore, with said first implant drill remaining therein, to confirm proper angulation of said initial bore;
   (f) removing said first implant drill from said initial bore upon confirming said proper angulation, and collecting bone tissue on threads of said first implant drill in a sterilized container;
   (g) manually driving one or more implant drills that has an increased diameter from said first implant drill using said manual driver to expand said initial bore by turning said manual driver clockwise and counter clockwise until obtaining a final bore having a desired diameter, removing said one or more implant drills, and collecting bone tissue on threads of said one or more implant drills into said container;
   (h) placing collected bone tissue into said final bore; and
   (i) placing a dental implant into said final bore that is filled with said collected bone tissue.

2. The method of claim 1, wherein said collected bone tissue is not washed by water or dehydrated.

3. The method of claim 1, wherein in step (h) said collected bone tissue fills in about 30% to about 50% of an interior of said final bore.

4. The method of claim 1, wherein in step (g) the method further comprises using one or more rotational bone expander to expand said initial bore.

5. The method of claim 1, wherein in step (h) said collected bone tissue is mixed with human allograft tissue prior to placing into said final bore.

* * * * *